United States Patent [19]
Young, David E. et al.

[11] Patent Number: 5,000,170
[45] Date of Patent: * Mar. 19, 1991

[54] ADJUSTABLE BIPIVOTAL HINGE WITH INTERDIGITATING ABUTMENT PLATES

[75] Inventors: Young, David E., Watlington; Kenneth P. Davis, Hillington; David J. Jackson, Witney, all of England

[73] Assignee: Protectair Limited, Abingdon, England

[ * ] Notice: The portion of the term of this patent subsequent to Nov. 21, 2006 has been disclaimed.

[21] Appl. No.: 304,499

[22] Filed: Jan. 31, 1989

[30] Foreign Application Priority Data

Feb. 2, 1988 [GB] United Kingdom ............... 8802288

[51] Int. Cl.$^5$ .......................... A61F 3/00; A61F 5/00
[52] U.S. Cl. ................ 128/80 C; 128/80 F; 128/88; 16/371; 16/239; 623/39
[58] Field of Search .............. 128/80 C, 88, 80 F, 128/80 H, 80 R, 80 B, 80 J, 89 R, 89 A; 623/39; 16/371, 375, 239, 235, 368; 2/22, 24; 403/70

[56] References Cited

U.S. PATENT DOCUMENTS

| | | | |
|---|---|---|---|
| 1,689,664 | 10/1928 | Covell | 16/371 |
| 1,693,992 | 12/1928 | Peterson | 16/371 |
| 3,350,719 | 11/1967 | McClure | 2/22 |
| 3,370,977 | 2/1983 | Mauldin et al. | 128/80 F |
| 3,552,786 | 1/1971 | Schmid | 287/100 |
| 3,958,569 | 5/1976 | Vosburg | 128/80 C |
| 4,245,629 | 1/1981 | Cummins | 128/80 C |
| 4,249,524 | 2/1981 | Anderson | 128/80 C |
| 4,323,059 | 4/1982 | Rambert et al. | 128/80 C |
| 4,337,764 | 7/1982 | Lerman | 128/80 F |
| 4,407,276 | 10/1983 | Bledsoe | 128/80 C |
| 4,489,718 | 12/1984 | Martin | 128/80 C |
| 4,502,472 | 3/1985 | Pansiera | 128/80 F |
| 4,520,802 | 6/1985 | Mercer et al. | 128/80 F |
| 4,524,764 | 6/1985 | Miller et al. | 128/80 C |
| 4,538,393 | 9/1985 | Michell | 16/371 |
| 4,573,455 | 3/1986 | Hoy | 128/80 C |
| 4,599,998 | 7/1986 | Castillo | 128/77 |
| 4,602,627 | 7/1986 | Vito et al. | 128/80 C |
| 4,620,532 | 11/1986 | Housewerth | 128/80 C |
| 4,727,861 | 3/1988 | Yeomans et al. | 128/80 C |
| 4,777,941 | 10/1988 | Borig et al. | 128/80 C |
| 4,817,588 | 4/1989 | Bledsoe | 128/80 C |
| 4,881,299 | 11/1989 | Young et al. | 128/80 C X |

FOREIGN PATENT DOCUMENTS 2182714 5/1987 United Kingdom ............... 128/88

OTHER PUBLICATIONS

Anderson, International Application PCT/US81/0066, published Aug. 19, 1982 (Pub. No. WO 82/02658).
European patent application 82105576.1 (Publication 0070411).
European patent application 85308859.9 (Publication 0184453).
German published application (Offenlegungsschrift) 2733205.

Primary Examiner—Richard J. Apley
Assistant Examiner—Jennifer L. Doyle
Attorney, Agent, or Firm—Tilton Fallon Lungmus

[57] ABSTRACT

An orthopedic and orthotic bipivotal hinge assembly having a hinge body and a pair of coplanar and independently-pivotal hinge arms. The proximal end portions of the hinge arms are disposed within the hinge body and have at least one set of interdigitating end plates defining an arrangement of abutment surfaces that are coplanar with each other, face generally in the same direction, and are disposed in side-by-side relation, when the arms are in first positions of adjustment (e.g., extension). In one embodiment, a single set of interdigitating plates with one such arrangement of abutment surfaces is provided; in a second embodiment two sets of interdigitating plates with two arrangements of abutment surfaces for controlling both extension and flexion are provided. Continuously variable extension and/or flexion control is achieved by an adjusting screw, or a pair of adjusting screws, carried by the hinge body.

8 Claims, 2 Drawing Sheets

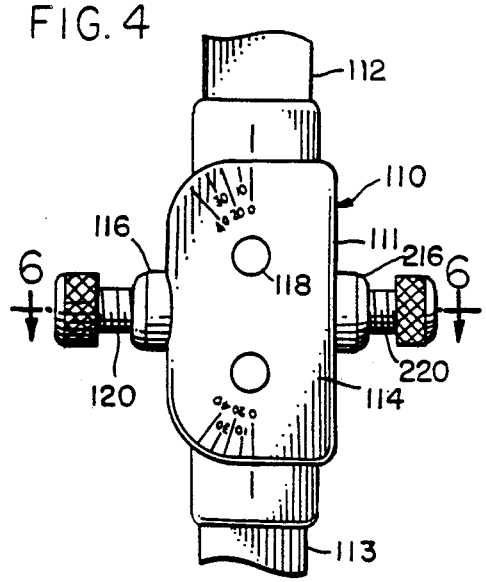
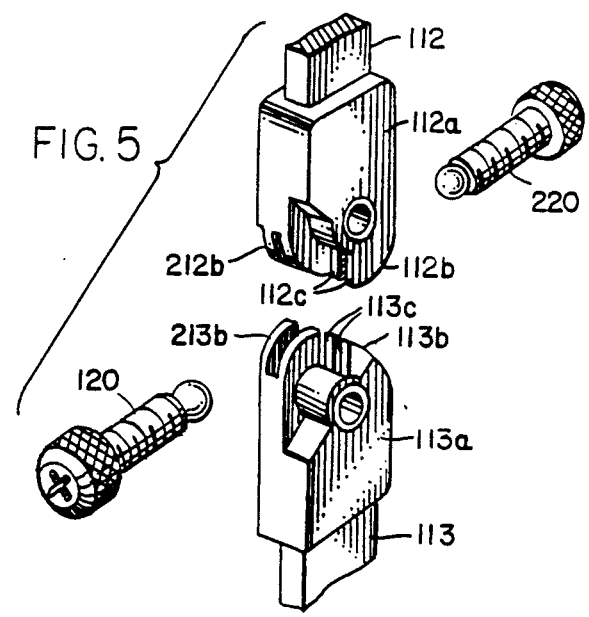
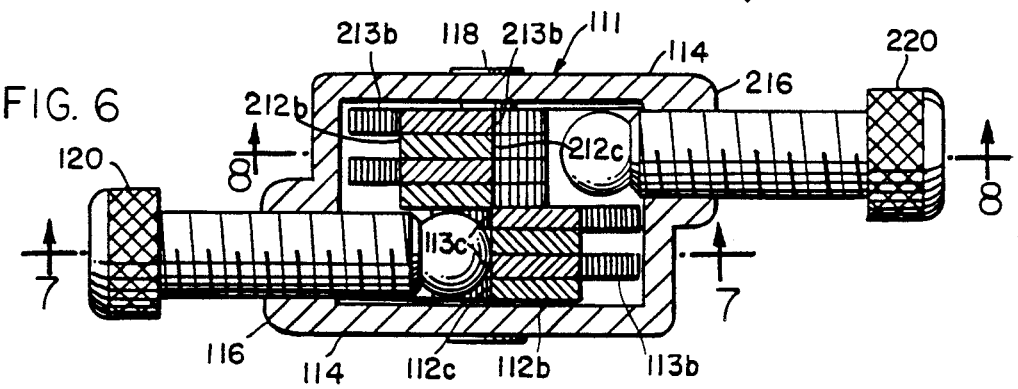
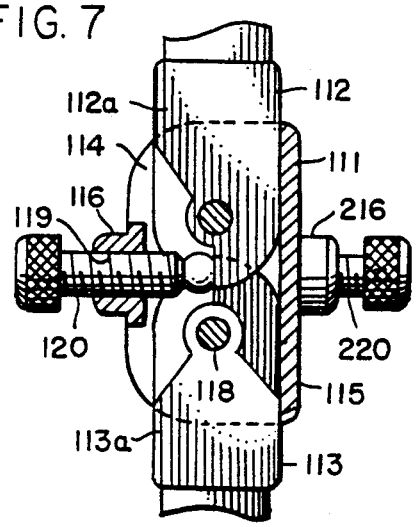
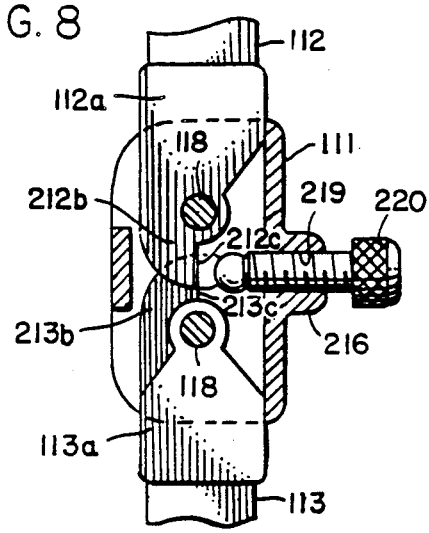

ADJUSTABLE BIPIVOTAL HINGE WITH INTERDIGITATING ABUTMENT PLATES

FIELD OF THE INVENTION

The present invention relates generally to bipivotal orthopaedic and orthotic hinge mechanisms or assemblies which are used in braces of various kinds.

Orthopaedic and orthotic hinges vary considerably in design and function. They are employed at joints, such as the knee or elbow, and their function is usually to supplement or partially substitute for the weight-bearing and motional characteristics of these joints. They are generally used in pairs with one hinge fitted laterally and the other fitted medially across the joint.

Orthopaedic and orthotic hinges are of two main types. The first employs a single pivot and is generally described as uniaxial or unipivotal; this type is quite commonly used in knee braces fitted in the practice of sports medicine, often following damage to the ligaments of the knee. Uniaxial hinges have also been used in lower leg walking devices for fractures of the foot. Such devices are used instead of short leg walking casts. In biomechanical terms, single pivot hinges are unphysiological when used at the knee because the knee does not move as a simple pivot hinge.

The second type of hinge mechanism has a central mount or hinge body which bears two pivots. The hinge arms are mounted one on each pivot and may either be independently pivotal or interconnected by gear teeth for coordinated pivotal action. In mechanical terms, a geared two pivot mechanism loses one degree of freedom when compared with two pivots which are not geared together. Geared two pivot hinges are also unphysiological when used at the knee because they effectively offer a single pivot point which migrates rearwardly when the hinge is moved from fully extended to fully flexed condition.

Two pivot hinge mechanisms in which the pivots or hinge arms are not geared together but are independently pivotal with respect to the hinge body may be called true bipivotal hinges, or by some authors, true biaxial hinges. They are considered to offer good tracking of the human knee joint as the femoral condyles glide over the tibial plateau when the leg is extended from a fully flexed position. Such a hinge assembly may be provided with a stop for preventing hyperextension of the hinge arms.

We know of few commercially available examples of true bipivotal hinges and have found relatively few references in the published art. One construction is believed to be based on Anderson U.S. Pat. No. 4,249,524 and published International Application WO 82/02658 (published Aug. 19, 1982). While the U.S. patent discloses a bi-pivotal hinge, it is believed that such hinge has unphysiological operating characteristics. The pivots are widely spaced to an extent that would tend to produce a pistoning action of the joint or limb in relation to the orthosis, an action that is undesirable especially in a damaged knee or in a knee which has recently undergone surgical repair or in a leg where there is a fracture. In the published International Application, the hinge differs as far as terminations of the hinge bars are concerned, but the drawings still reveal widely-separated pivots. Although Anderson briefly mentions stops in the published application, there is no disclosure of a variable motion limiting system.

In U.S. Pat. No. 4,337,764 and European patent publication 0059472, Lerman discloses an adjustment mechanism for two-pivot geared hinges. The system depends on a hinge backplate with an arcuate slot in which there are located two compression screw sets lying outside either side of the hinge arm. Since the hinge arms are geared together and cannot move independently, the disclosed construction is not a true bipivotal hinge.

Mercer and Aaserude U.S. Pat. No. 4,520,802 discloses another bipivotal hinge featuring wide pivot spacing. The disclosure includes a motion control system based on indexing blocks. The system is discontinuous and incapable of infinite variable adjustment, leaving the user subject to the values of the index blocks made available by the manufacturer.

Most hinges have securing means for fixing them directly or indirectly to a limb. Where a hinge mechanism is to be retained on the limb by a cast, it will usually have hinge arms which terminate in structures adapted for embedding in the cast and commonly termed headplates or anchor plates. Orthotic hinges are normally supplied as independent units which are subsequently either built directly onto plastic orthoses or fitted to mating side arms called "steels" and then incorporated into calipers. Lower limb orthoses in particular are generally secured to the limb with straps.

Observations made under widely varying conditions in several different countries lead us to the conclusion that strap-on devices have more potential for relative motion between limb and device than do casts. This is primarily because casts are inherently rigid and constitute a fully circumferential integrated structural unit, whereas strap-on devices are usually made from a combination of soft goods and flexible materials and cannot form an integrated circumferential structure. We believe, therefore, that in the design of motion control mechanisms for orthopaedic and orthotic hinges, adjustment systems should be capable of continuous or infinite variation between adjustment extremes. This ensures the proper compensation for relative motion between the leg and the brace when such hinges are used with strap-on braces can be achieved.

Other authors have described means for limiting motion in orthopaedic hinges but all too frequently the type of hinge selected is unsuitable for the joint being braced, especially when complex motion is involved such as that of the knee joint. Thus, the motion control mechanism in Houswerth U.S. Pat. No. 4,620,532 has the advantage of compactness but the uniaxial hinge is not well suited for knee bracing because no uniaxial hinge is known to track the human knee satisfactorily. In Castillo U.S. Pat. No. 4,599,998, the motion control system involves a ratchet and is also compact but is applied to a geared two-pivot system which again has known disadvantages in properly tracking the human knee.

Another type of adjustment mechanism for a two-pivot geared hinge is found in a construction marketed by Rolyan Manufacturing Co., Menomonee Falls, Wis., U.S.A. Two screws located in the top of the hinge body are used to limit travel of one hinge arm in flexion and extension, respectively. This is achieved by driving the screws down into the body so that the ends strike the top edges of the hinge arms. The screws remain exposed at all times and require a locking nut to maintain adjustment.

In our co-pending British patent application 8510028, published May 20, 1987 as GB 2,182,714A, and U.S.

patent application No. 853,962, filed Apr. 21, 1986, we disclose a true bipivotal knee hinge which employs closely-spaced pivots. Each hinge arm includes a carrier with two cam abutment stops arising from it, one on either side of and close to its pivot. Motion limiting screws, one to control flexion and the other to control extension, are provided for each pivot.

Co-pending, co-owned U.S. patent application No. 156,250, filed Feb. 16, 1988, and British application 8703823, disclose a true bipivotal hinge mechanism having a single adjusting screw for controlling the maximum degree of extension of the hinge arms.

Other patents representing the state of art are U.S. Pat. Nos. 3,350,719, 4,407,276, 3,958,569, 4,370,977, 4,489,718, 4,323,059, 3,552,786 and 4,502,472.

SUMMARY OF THE INVENTION

An important aspect of this invention lies in providing an orthopaedic and orthotic hinge mechanism that has all of the functional advantages of a true bipivotal hinge mechanism and, in addition, provides more effective blocking at desired limits of extension and/or flexion without risk of loss of adjustment at maximal physiological loads. Such advantages are achieved with a mechanism that is relatively compact and, therefore, particularly useful for so-called functional or sports braces and for calipers.

Briefly, the adjustable bipivotal hinge assembly includes a hinge body having a pair of side walls spaced part to define a cavity or chamber for receiving the proximal end portions of a pair of hinge arms. The arms are pivotally connected to the body for independent movement of such arms between flexion and extension.

A distinctive feature of the assembly is that the proximal end portions of the hinge arms together provide at least one set of interdigitating end plates. The end plates of each set define an arrangement of abutment surfaces that are coplanar with each other, face generally in the same direction, and are disposed in side-by-side relation, when the arms are in first positions of adjustment (e.g., extension).

The hinge body also includes a screw housing, or a pair of screw housings, containing screw means forming adjustable stops for the abutment surfaces of both of the arms for limiting pivotal movement of such arms in the direction of extension, or of flexion, or both. In one embodiment, a single screw forms an adjustable stop for the abutment surfaces of one set of interdigitating end plates for selectively controlling maximum extension or flexion of the arms. In a second embodiment, a pair of adjustment screws are positioned to contact two arrangements of abutment surfaces provided by two sets of interdigitating end plates for selectively controlling the maximum limits of both extension and flexion.

Other features, advantages, functions, and objects of the invention will become apparent from the specification and drawings.

DRAWINGS

FIG. 4 is a side elevational view of a second embodiment of the invention.

FIG. 5 is an exploded perspective view of the principal pivot-controlling elements of the second embodiment.

FIG. 6 is an enlarged cross sectional view taken along line 6—6 of FIG. 4.

FIG. 7 is a vertical sectional view taken along line 7—7 of FIG. 6.

FIG. 8 is a vertical sectional view taken along line 8—8 of FIG. 6.

DETAILED DESCRIPTION OF PREFERRED EMBODIMENTS

Figure 1:
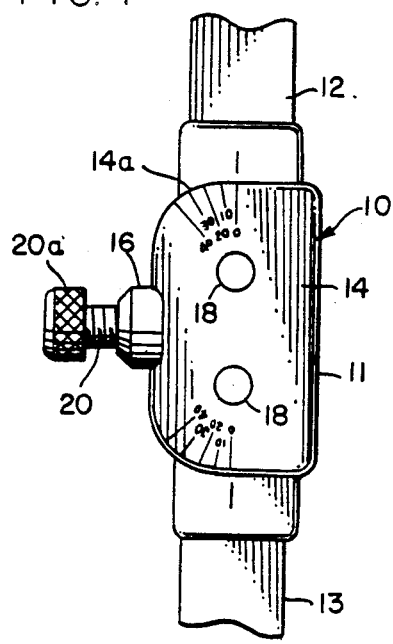
FIG. 1 is a side view of a hinge assembly embodying this invention.
Figure 2:
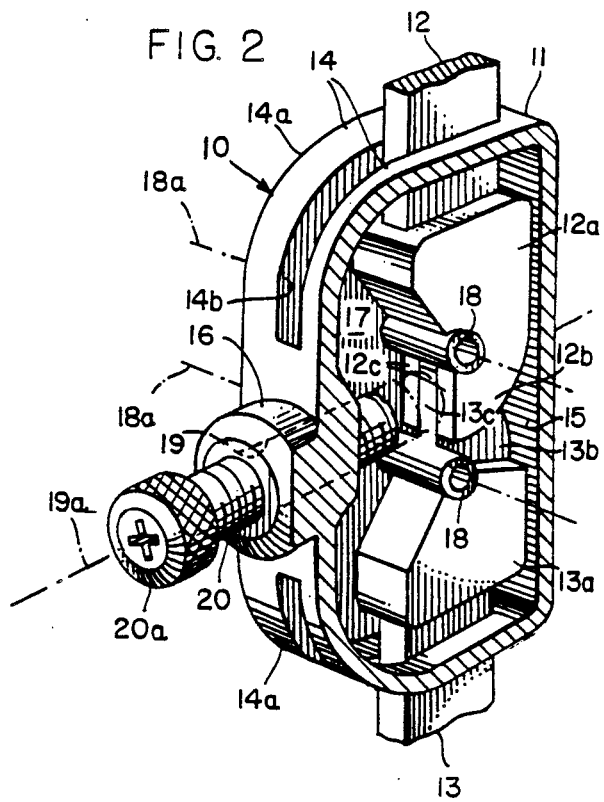
FIG. 2 is an enlarged fragmentary perspective view illustrating the interior mechanism of the bipivotal hinge assembly of FIG. 1.
Figure 3:
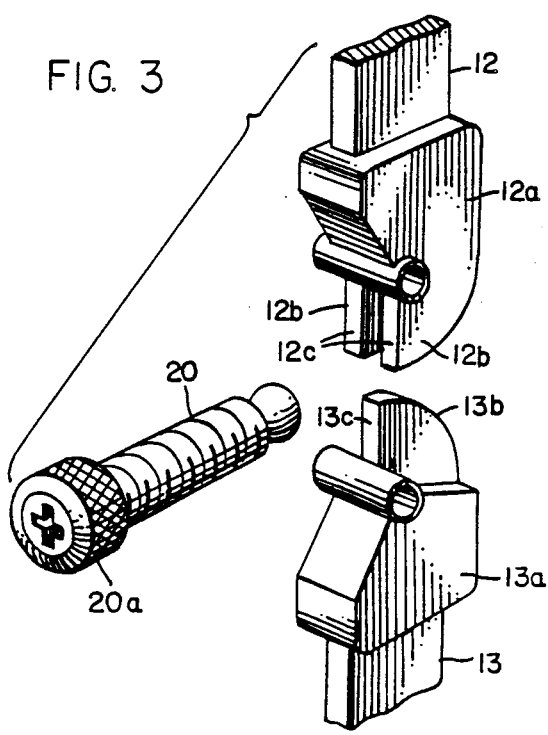
FIG. 3 is an exploded perspective view of the principal pivot-limiting elements of the mechanism.

Referring to FIGS. 1-3 of the drawings, the numeral 10 generally designates a bipivotal hinge assembly that includes a hinge body 11 and a pair of hinge arms 12 and 13. The hinge body comprises a pair of vertical side walls 14 joined by an anterior or front wall 15. The posterior corners of the side walls are rounded at 14a and an enlarged boss or housing 16 joins the posterior portions of the side walls. As shown most clearly in FIG. 2, certain components such as the screw housing 16, anterior wall 15, and side walls 14 may be integrally formed; alternatively, such parts may be formed separately and secured together by any suitable means. The hinge body may be formed of any material having sufficient strength and rigidity. Metals such as steel, titanium, and aluminum are appropriate, but high-strength rigid plastics may also be used. While in the embodiment shown, screw housing 16 is provided at the posterior end of the hinge body and no screw housing is located along anterior wall 15, such arrangement is for illustrative purposes only and, if desired, the arrangement may be reversed with the screw housing located along the anterior end of the body and omitted from the posterior end. Furthermore, as revealed by the second embodiment illustrated in FIGS. 4-8 to be described hereinafter, the hinge body may be provided with two screw housings, one projecting from the anterior end of the body and the other from its posterior end.

Side walls 14 have opposing planar inner surfaces 14b that are spaced apart to define a cavity or chamber 17 for receiving the proximal end portions 12a and 13a of hinge arms 12 and 13. Except in the respects described below, the hinge arms 12 and 13 are conventional, being formed of flat strips or bars of steel, aluminum, or other rigid materials having similar properties. The distal ends of the arms (not shown) are suitably adapted to fit headplates (as shown, for example, in U.S. Pat. Nos. 4,559,935 and 4,467,792), brace plates, or other known means for securing such arms to the limb of a patient.

The proximal end portions 12a and 13a of the hinge arms together provide a set of interdigitating end plates 12b and 13b that extend along parallel vertical planes. Three such end plates are shown in FIGS. 2 and 3, with plate 13b fitting between parallel plates 12b; however, a greater number of interdigitating plates may be provided if desired. The proximal end portions 12a and 13a of the hinge arms are pivotally connected to the body 11 by means of pivot shafts or inserts 18 carried by side walls 14. As shown in FIG. 2, the shafts 18, and hence the pivot axes 18a of hinge arms 12 and 13, are generally horizontal, parallel to each other, and normal to the planes of side walls 14. The shafts 18 extend through the proximal end portions of the hinge arms and support the arms for independent pivotal movement between positions of flexion and extension.

The interdigitating end plates 12b and 13b provide an arrangement of abutment surfaces 12c and 13c that, as shown in the drawings, generally lie in planes that extend along pivot axes 18a. When the arms of the bipivotal assembly are in one of their positions of adjustment—preferably in positions of extension as shown in FIG. 2—such abutment surfaces are coplanar with each other, face generally in the same direction, and are disposed in side-by-side relation. Where screw housing 16 is located at the posterior end of hinge body 11, surfaces 12c and 13c face posteriorly (FIGS. 2, 3). Of particular importance is the fact that the abutment surfaces 12c and 13c of the interdigitating end plates 12b and 13b are disposed immediately adjacent to each other so that together they form a nearly continuous planar surface when the arms 12 and 13 are so extended.

Screw housing 16 has a threaded bore 19 with an axis 19a that is equidistant from pivot axes 18a and, in the embodiment of FIGS. 1-3, is also equidistant from the opposing surfaces 14b of the side walls 14a with which it is parallel. Adjustment means in the form of an adjusting screw 20 is threadedly received in bore 19. The inner end of the screw is positioned to contact the abutment surfaces of the interdigitating or interleaving end plates 12b and 13b to control the limits of movement of the arms in one direction (extension, as depicted in FIGS. 1-3). It will be seen that axis 19a (which is also the axis of adjustment screw 20) is normal to the common plane of abutment surfaces 12b and 13b when the arms are in positions of extension, that is, when the arms are aligned at 180 degrees (FIG. 2). As the adjusting screw 20 is screwed inwardly, it will effectively block the hinge arms from reaching positions of full extension. The extension-blocking capability is infinitely variable between positions of full extension and of partial extension. The usual amount of extension blocking that would be imparted to preferred embodiments of the hinge would be approximately 60 degrees which exceeds the normal range of extension blocking employed following repairs to the cruciate ligaments of the knee.

Screw 20 may be provided with an enlarged head or cap 20a which is useful in limiting the extent of inward threading of the screw and therefore prevents any possibility of jamming the hinge mechanism. Since the adjusting screw 20 and housing 16 are disposed on the posterior end of hinge body 11 in the embodiment of FIGS. 1-3, and since the axis of the screw is equidistant from pivot axes 18a, such elements would not be expected to contact the leg of a wearer (or other persons or objects) during normal use of the hinge assembly.

In a preferred embodiment of the invention, adjusting screw 20 may have a diameter of 6 mm with a 1 mm pitch. Applying such proportions to the embodiment illustrated, there would never be less than about 8 mm of thread in the bore 19 of housing 16; hence, the load transmitted to the abutment surfaces of the interdigitating end plates 12b and 13b would never be distributed over a thread length of less than:

$8\pi d = 150.9$ mm

Although migration of the adjusting screw in its threaded bore would be highly unlikely, we would prefer to use a resin patch on the thread to insure against any possibility of such unintended migration.

The interdigitating of end plates 12b and 13b has the effect of maximizing the areas of contact between the adjusting screw and the abutment surfaces and of avoiding the risk that the screw might become jammed or wedged between the end plates when the screw is threaded inwardly. Ideally, the plates should maintain an interdigitating relation over the full range of pivotal movement of the arms.

The embodiment of FIGS. 4-8 is similar to the one already described except that two sets of interdigitating end plates are provided, each set with its own arrangement of abutment surfaces, and two adjusting screws are provided for selectively controlling maximum limits of both extension and flexion.

Hinge assembly 110 includes a hinge body 111 with side walls 114, anterior wall 115, and posterior wall or screw housing 116. As in the first embodiment, pivot shafts 118 extend through and between the side walls to support arms 112 and 113 for pivotal movement between positions of extension and flexion. Screw 120, with its axis disposed equidistant from the pivot axes of shafts 118 and extending normal to the common plane of such shafts, is threadedly received in the bore 119 of screw housing 116.

As shown most clearly in FIGS. 5 and 6, the proximal end portions 112a and 113a of the hinge arms include a first set of interdigitating end plates 112b and 113b. The interdigitating plates define abutment surfaces 112c and 113c that bear the same relationships to each other and to adjustment screw 120 as described in connection with the embodiment of FIGS. 1-3. Thus, when the hinge arms 112 and 113 are in one selected position of adjustment (extension, as shown in the drawings), abutment surfaces 112c and 113c are coplanar with each other, face generally in the same direction (posteriorly), and are disposed in side-by-side relation.

Unlike the first embodiment, however, the embodiment of FIGS. 4-8 includes a second set of interdigitating or interleaving end plates 212b and 213b that are disposed laterally with respect to end plates 112b and 113b of the first set. The plurality of end plates of the second set define abutment surfaces 212c and 213c that are coplanar of each other, disposed in side-by-side relation, and face in the same direction (anteriorly) when the hinge arms are in a selected position of angular adjustment (extension). The two sets of interdigitating end plates (112b, 113b on one hand, and 212b, 213b on the other) are disposed laterally to each other and are positioned and arranged to contact adjusting screws 120 and 220. Like screw 120, adjusting screw 220 has its axis equidistant from the pivot axes of the hinge arms 112 and 113; however, screw 220 extends anteriorly from threaded bore 219 of screw housing 216 (FIG. 8) whereas adjusting screw 120 projects posteriorly from its screw housing. The axes of the two laterally-spaced screws are parallel to each other and lie in the same horizontal plane.

The duplexed arrangement permits selective adjustment of maximum flexion as well as maximum extension. Posterior screw 120 may be adjusted to control the limits of extension of arms 112 and 113 whereas screw 220 may be adjusted to control the limits of flexion of those arms. The advantages of interdigitation of the end plates are the same as previously described, but with such advantages being associated with position control of the two hinge arms in relation to both extension and flexion.

While in the foregoing we have disclosed embodiments of the invention in considerable detail for purposes of illustration, it will be understood by those skilled in the art that many of these details may be varied without departing from the spirit and scope of the invention.

We claim:

1. An adjustable bipivotal hinge assembly comprising a hinge body having a pair of side walls with spaced opposing inner surfaces; first and second hinge arms having a pair of proximal end portions received between said opposing inner surfaces of said side walls; pivot means pivotally connecting said hinge arms to said hinge body for independent pivotal movement of each of said arms between flexion and extension about a pair of parallel pivot axes; said proximal end portions of said first and second hinge arms together providing a set of interdigitating end plates defining an arrangement of abutment surfaces that generally lie in planes extending in directions along said pivot axes; said abutment surfaces of said interdigitating end plates being coplanar with each other, facing generally in the same direction, and being disposed in side-by-side relation, when said arms are in a selected position of adjustment; said hinge body also including a screw housing having a threaded bore normal to a plane parallel with and extending between said pivot axes; and screw means threadedly and adjustably received in said bore for contacting said abutment surfaces of both of said arms for limiting pivotal movement in a direction of flexion or extension.

2. The assembly of claim 1 in which said axis of said threaded bore is equidistant from said pivot axes of said hinge arms.

3. The assembly of claim 1 in which said selected position of adjustment of said arms is a position of extension.

4. The assembly of claim 3 in which the common plane of said abutment surfaces extends through both of said pivot axes when said arms are in extension.

5. The assembly of claims 1, 2 or 3 in which said hinge body has anterior and posterior ends; said abutment surfaces facing posteriorly when said arms are in extension; said screw housing and screw means being located at said posterior end for adjustably limiting pivotal movement of said hinge arms in directions of extension.

6. The assembly of claims 1, 2 or 3 in which said hinge body has anterior and posterior ends; said abutment surfaces facing anteriorly when said arms are in extension; said screw housing and screw means being located at said anterior end for adjustably limiting pivotal movement of said hinge arms in directions of flexion.

7. The assembly of claim 6 in which said proximal end portions of said first and second hinge arms have a second set of interdigitating end plates defining a second arrangement of abutment surfaces; said abutment surfaces of said second arrangement facing anteriorly when said arms are in said selected positions of adjustment; said hinge body having a second screw housing provided at said anterior end; said second screw housing also having a second threaded bore with its axis normal to said plane extending between and parallel with said pivot axes; and second screw means threadedly and adjustably received in said second bore for contacting said second arrangement of abutment surfaces and for adjustably limiting pivotal movement of said hinge arms in directions of flexion.

8. The assembly of claim 7 in which said axes of said first-mentioned bore and said second bore are spaced laterally apart between said side walls of said body; said second arrangement of abutment surfaces being disposed laterally in relation to said first-mentioned arrangement of abutment surfaces.

* * * * *